United States Patent [19]

McCoy et al.

[11] Patent Number: 4,735,939

[45] Date of Patent: Apr. 5, 1988

[54] INSECTICIDAL ACTIVITY OF STAUROSPORINE

[75] Inventors: Karen M. McCoy, Midland, Mich.; Christopher J. Hatton, Benicia, Calif.

[73] Assignee: The Dow Chemical Company, Midland, Mich.

[21] Appl. No.: 19,909

[22] Filed: Feb. 27, 1987

[51] Int. Cl.$^4$ .................................... A01N 43/00
[52] U.S. Cl. .................................................. 514/211
[58] Field of Search ......................................... 514/211

[56] References Cited

U.S. PATENT DOCUMENTS 4,107,297 8/1978 Omura et al. .................. 424/122

OTHER PUBLICATIONS

Omura, Satoshi et al., Journal of Antibiotics, XXX, No. 4, pp. 275-282 (1977).
Tamaoki, Tatsuya et al., Biochemical and Biophysical Research Communications, vol. 135, No. 2, pp. 397-402 (1986).
CA 101(7):55460 (1984).
CA 100(13):103700r (1984).
CA 99(17):139599q (1983).
CA 98(25):215863t (1983).
CA 98(19):161000p (1983).
CA 90(13):104185p (1979).

*Primary Examiner*—Allen J. Robinson
*Attorney, Agent, or Firm*—S. Preston Jones; Ronald G. Brookens

[57] ABSTRACT

A method for inhibiting insects by contacting insects or habitat thereof with an effective amount of staurosporine.

19 Claims, No Drawings

INSECTICIDAL ACTIVITY OF STAUROSPORINE

BACKGROUND OF THE INVENTION

Staurosporine is an alkaloid compound produced by fermentation of a suitable microorganism belonging to the genus Streptomyces. A suitable strain for staurosporine production is Streptomyces AM-2282 (NRRL 11184) as described in U.S. Pat. No. 4,107,297 and Ger. Offen. DE No. 2,754,326. Information is also available on the molecular structure of staurosporine (e.g., see Furusaki, Akio, et al., *Bull. Chem. Soc. Jpn.*, 55 (12), pp. 3681–3685, and Furusaki, Akio, et al., *J. Chem. Soc. Chem. Commun.*, (18), pp. 800–801. Staurosporine is known to have antimicrobial activity (primarily against fungi) and is also known to have hypotensive and antiedema activities in rats. Heretofore, insecticidal activity has been unknown for staurosporine.

SUMMARY OF THE INVENTION

The present invention is directed to a method for inhibiting insects which comprises contacting insects or the habitat thereof with an insecticidally effective amount of staurosporine.

The present invention is also directed to an insecticidal composition comprising an inert carrier or insecticide adjuvant and an insecticidally effective amount of staurosporine. It is contemplated that both inert carriers and insecticide adjuvants simultaneously can be present in the compositions of the present invention.

The present invention is further directed to a method for inhibiting insects which comprises contacting insects or the habitat thereof with a composition containing an inert carrier or insecticide adjuvant and an insecticidally effective amount of staurosporine.

As used herein, the term "inhibiting" or "inhibits" refers to suppression, control, inactivation, kill, or any other adverse interference with the normal life processes of insects; the term "insecticidally effective amount" refers to that amount of staurosporine which results in inhibition of insects when the staurosporine is contacted with the insects or the habitat thereof.

DETAILED DESCRIPTION OF THE INVENTION

Staurosporine has the following structure:

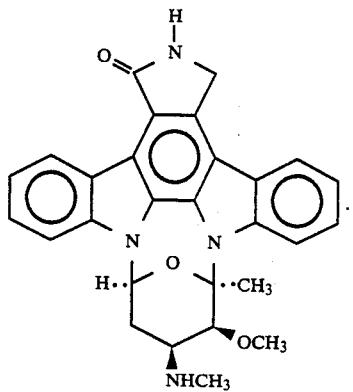

Staurosporine is known to be produced by several strains of bacteria, particularly of the Streptomyces genus. The whole fermentation broth of such staurosporine-producing organism, after a suitable fermentation period, can be applied directly to insects or habitat thereof for insecticidal control. A suitable fermentation period will vary with specific fermentation or growth conditions and with the strain of staurosporine producing organism. Typically, for convenience, such organisms are grown to stationary phase in order to obtain sufficient quantities of the active staurosporine; however, sufficient amounts of staurosporine can also be typically produced during the exponential or logarithmic growth phase.

Such whole broth containing staurosporine can optionally be further fractionated and the active staurosporine further purified.

For some insects, staurosporine must be applied in concentrations greater than what is typically present in whole fermentation broth in order to inhibit such insects. Also purified staurosporine and/or stabilized staurosporine may be required to inhibit some insects.

It is also contemplated that staurosporine, that is chemically synthesized, is within the scope of the present invention.

Staurosporine has been shown to have low persistence and "quick knockdown" insecticidal activity. Because of these properties, staurosporine is particularly suitable for the inhibition of insect pests inside houses, barns, warehouses, public buildings, and the like. When used in such locations, staurosporine inhibits cockroaches, such as the German cockroach, American cockroach, and brownbanded cockroach; beetles, such as the black-carpet beetle, confused flour beetle, sawtooth grain beetle, and larder beetle; spiders; silverfish; bedbugs; fleas, such as those on bedding used by household pets, and flea larvae; mosquitoes; boxelder bugs; mites; ants; centipedes; and flies, such as hornfly, stable fly, facefly, and the common housefly. In addition, staurosporine is also useful for the inhibition of lice and ticks and other insects parasitic to animals.

Staurosporine is effective for the inhibition of the many insect pests found on the roots or aerial portions of growing plants. Such insect pests include aphids; scale; mites; white flies; and chewing and sucking insects such as leafhopper, southern armyworm, twospotted spidermite, cotton aphid, cabbage looper, western spotted cucumber beetle, bollworm, codling moth, beet armyworm, and tobacco budworm.

Staurosporine, when applied to plants, plant parts, and their habitats to protect the plants from the attack of insect pests, exhibits residual inhibition of the insects over a relatively short period of time thereby not having appreciable build-up in the environment.

As appreciated by one skilled in the art, insecticidally effective amounts of staurosporine will vary depending upon the particular application and circumstances concerning such application. However, for most agricultural applications, insecticidally effective amounts of staurosporine will typically vary between about 10 grams and about 4 kilograms per hectare, preferably between about 100 grams and about 2 kilograms per hectare and most preferably between about 250 grams and about 1 kilogram per hectare.

As appreciated in the art, staurosporine will vary in effectiveness from one insect species to another. That is, dosages of staurosporine effective against one species may have to be increased in order to be effective against different or more resistant species.

In some procedures, staurosporine can be vaporized or sprayed or distributed as an aerosol into the air, or onto surfaces in contact with the air. In such applications, staurosporine manifests the useful properties hereinbefore described.

The methods of the present invention comprise contacting an insect with an insecticidally effective amount of staurosporine.

The contacting can be effected by application of staurosporine to the habitat of the insects. Representative habitats include soil, air, water, food, vegetation, inert objects, stored matter such as grains, other animal organisms, and the like. The inhibition can be lethal, immediately, or with delay, or can be a sublethal one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inhibition of an insect by the application of an insecticidally effective amount of the staurosporine compound is critical to the method of the present invention. The compound can sometimes be employed in unmodified form. Frequently, however, for easier application, the compound is modified by the employment with it of a pesticidal adjuvant or inert carrier therefor. Staurosporine is insoluble in water but is relatively soluble in oils, including plant essential oils. Therefore, the practical enjoyment of the beneficial utilities of the present compounds often requires that staurosporine be admixed with one or more pesticidal adjuvant substances, and the resulting compositions are included within the present invention.

The compositions can be formulated in various forms, such as emulsifiable concentrates, wettable powders, flowable suspension dusts, granules, microencapsulated granules, fine granules, oil sprays, aerosols, heating fumigants (e.g, mosquito coils, electric mosquito killer mat, etc.), fogging mists, non-heating fumigants and poisonous baits and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with staurosporine so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising staurosporine, an organic liquid as a solvent and carrier therefor, and a propellant material. Numerous other embodiments will become apparent to those skilled in the art in view of the teachings set forth hereinbelow.

The exact concentration of staurosporine in a composition thereof with an adjuvant therefor can vary; it is only necessary that the active compounds be present in a sufficient amount so as to make possible the application of an insecticidally effective dosage. Generally, for practical applications, the staurosporine can be broadly applied to insect pest organisms or their habitat in compositions containing from about 1 percent to about 50 percent by weight of the active staurosporine compound.

In the preparation of dust compositions, the product can be compounded with any of the finely divided carrier solids such as pyrophyllite, diatomaceous earth, gypsum and the like. In such operations, the finely divided carrier is ground or mixed with active staurosporine compound, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, one of the compounds or a dust concentrate composition containing such compound can be incorporated in intimate mixture with surface-active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the staurosporine can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the staurosporine compound or a composition containing the compound is applied to the insects to be inhibited directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane. The present invention also comprehends the employment of compositions comprising staurosporine, an adjuvant, and one or more other biologically active materials, such as insecticides, fungicides, miticides, bactericides, nematocides, and the like.

A preferred and especially convenient means for the application of one or more of the present products comprises the use of a self-pressurized pack formulation which can be used, for example, as a space or surface spray. Such a formulation can comprise staurosporine, an organic liquid as a solvent and vehicle therefor, and a propellant material which can be condensed and compressed gas or a substance which, at room temperature, is a gas under atmospheric pressure but which liquefies under super atmospheric pressure. Where the propellant material is of the latter type, the self-pressurized pack formulation is often spoken of as an aerosol. Representative propellants include propane, butane and nitrogen. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulations, see U.S. Pat. Nos. 1,892,750 and 2,321,023.

The present invention is further illustrated by the following examples; however, these examples should not be interpreted as a limitation upon the scope of the present invention. Unless indicated otherwise, all percentages are by weight.

EXAMPLE 1

A staurosporine producing strain of Streptomyces was grown in a suitable culture medium to stationary phase using the techniques substantially as described in Journal of Antibiotics, Vol. XXX, No. 4, April, 1977, pp. 275–282. The unmodified whole fermentation broth thus obtained was then freeze dried. Individual samples of the freeze dried whole broth (equivalent to 50 ml of original broth) were each reconstituted in 30 ml of distilled water and 0.5 ml of 5 percent surfactant (Triton X-155) in acetone immediately prior to use. In some circumstances, the samples were diluted; for example, a dilution factor of 2, 4, 8 or 16 means that the reconstituted sample was diluted to ½, ¼, ⅛ or 1/16 strength or concentration. Representative reconstituted samples prepared as described above where evaluated for insecticidal activity against beet armyworm ("BAW") species *Spodoptera exigua*, tobacco budworm ("TBW") species *Heliothis virescens*, and two-spotted spidermite ("2SSM") species *Tetranychus urticae* according to the following methods.

A. BAW and TBW Method

The activity of the reconstituted samples against BAW and TBW was determined in a leaf feeding experiment in which activity observed may have been due to contact or ingestion toxicity.

Cotton plants with their first and second true leaves fully expanded were dipped into the reconstituted broth and allowed to air dry. The leaves were excised from the plants and placed into petri dishes. Five late third instar larvae of BAW and TBW were applied to each leaf and the petri dish was covered with a lid. The plates were stored on trays in a plastic bag placed in an incubator at 78° F. for 5 days. After this time, the plates were examined for larval death and leaf consumption.

Results were expressed as percent mortality and notes were made on leaf consumption in the case of a late "kill".

B. 2SSM Method

One-leaf cotton plants with only their first true leaf (about 2 inches long) were infested overnight by placing a piece of lightly infested donor leaf from the 2SSM colony on their adaxial surface. At this time they were treated by dipping the leaf in, or spraying to run-off with the reconstituted broth.

Percentage efficacy was evaluated after 5 days by comparing the number of surviving mites on the treated plants with the survivors on a similar set of plants treated with the surfactant control only.

The results of the testing by use of the above-described method are shown in Table I.

TABLE I

| Sample No. | Dilution Factor | % Mortality for Organism: | | |
|---|---|---|---|---|
| | | BAW | TBW | 2SSM |
| 1 | Undiluted | 100 | 100 | 50 |
| 2 | Undiluted | 100 | 80 | 99 |
| 3 | Undiluted | 100 | 59 | 50 |
| 3 | 2 | 50 | 0 | 90 |
| 3 | 4 | 50 | 0 | 80 |
| 3 | 8 | 0 | 0 | 50 |
| 3 | 16 | 0 | 0 | 50 |

EXAMPLE 2

A staurosporine producing strain of Streptomyces was grown in a suitable culture medium to stationary phase using the techniques substantially as described in Journal of Antibiotics, Vol. XXX, No., 4, April, 1977, pp. 275–282.

About 400 ml of the whole fermentation broth thus obtained was centrifuged to separate the clear broth from the cells. The cells were then extracted with acetone and the clear broth was extracted with methyl isobutyl ketone. The acetone and methyl isobutyl ketone were removed from the extract containing the staurosporine to yield a solid extract. The solid extract was then dissolved in 2 ml of 5 percent Triton X-155 in acetone and then further diluted with distilled water to yield 50 ml of sample solution. A series of two-fold dilutions of the sample solution was then made in distilled water; up to 1 in 16. This dilution series of samples was N, N/2, N/4, N/8 and N/16; with N being equal to undiluted sample solution and N/16 being equal to the 1 in 16 dilution of the sample solution.

The sample solution and dilutions thereof, obtained as described above, were then tested for activity by using the following methods.

A. Contact Activity vs. TBW

Each different dilution was poured into an individual, respective, 10×35 millimeter (mm) petri dish containing a paper disc, drained and allowed to dry. A 0.25 inch plug of artificial diet was placed on a paper disc in the center of the dish. A late instar TBW larva was placed in each replicate and confined by replacing the lid (5 replicates were run at each treatment level). The dishes were stored in a plastic bag to maintain a high humidity, at 78° F. in an incubator. The larvae were examined for survival 4 days later.

B. Contact and Stomach Poison Test vs. BAW and TBW

This procedure was similar to that described in Example 1A, except that the leaves were harvested at 0 and 5 days post-treatment and infested with larvae to determine the residuality of the extract.

C. 2SSM Contact Activity

Two cotton plants with their first true leaf (about 2 inches long) were dipped in each dilution of the staurosporine and allowed to dry. Ten adult female 2SSM were carefully applied to each leaf by use of a camel hair brush. A similar set of plants were treated with a solvent blank (controls). Five days later the mites were counted and a percent reduction was calculated based upon the survival rate of the mites on the check plants.

D. 2SSM Systemic Activity

This procedure was similar to that described in Example 2C except that the dilutions of staurosporine were applied to the roots (5 ml) and the plant pot was maintained standing in a plastic butter dish. The results of the testing by use of the above-described methods are shown in Table II.

TABLE II
ACTIVITY SUMMARY OF PARTIALLY PURIFIED STAUROSPORINE

| | % Control | | | | |
|---|---|---|---|---|---|
| Type of Activity | N | N/2 | N/4 | N/8 | N/16 |
| Tobacco Budworm | | | | | |
| Contact | 60 | 40 | 0 | 20 | 20 |
| Contact/Stomach | | | | | |
| 0 time | 100 | 50 | 0/af* | 0 | 0 |
| 2 day | 0 | 0 | 0 | 0 | 0 |
| Beet Armyworm | | | | | |
| Contact/Stomach | | | | | |
| 0 time | 80 | 100 | 0 | 0 | 0 |
| 2 day | 0 | 0 | 0 | 0 | 0 |
| Two-spotted Spidermite | | | | | |
| Contact | 50 | 22 | 0 | 0 | 0 |
| Systemic | 0 | 10 | 0 | 10 | 0 |

*antifeedant - insect did not feed

EXAMPLE 3

The following example demonstrates the insecticidal activity of staurosporine using staurosporine in a form that is substantially chemically pure. The staurosporine was purified using procedures substantially similar to those described in Journal of Antibiotics, Vol. XXX, No. 4, April, 1977, pp. 275-282.

A. Methods

1. Leafhopper/parafilm test

The bottom of a small plastic petri dish was closed off with parafilm, then an access hole was made in the base of the petri dish. This petri dish was then placed, with the parafilm facing down, onto a 1 ounce pill cup which contained adult aster leafhoppers. A 5 percent sucrose solution containing staurosporine at the appropriate concentration was introduced into the petri dish via the access hole. Leafhopper mortality was determined after three days during which they had imbibed solution by sucking via the parafilm membrane. Five replicate cups were used at each concentration.

2. Tobacco budworm (Heliothis virescens) injection test

Larvae, weighing approximately 50 mg, were injected with a fresh acetone solution of staurosporine by use of a microliter syringe (vol. 0.5 $\mu$l). They were maintained individually in a small petri dish with a piece of artificial diet and observation was made 72 hours later for mortality or stunting. Five replicates were used at each dose level.

3. Tobacco budworm topical application test

This test was similar to test 2 except that the compound was applied externally to the larvae. Five replicates were used at each dose level.

B. Results

1. Leafhopper/parafilm in-vitro test

TABLE III

| Staurosporine Conc. (ppm) | % Control* |
|---|---|
| 400 | 86 |
| 200 | 97 |
| 100 | 87 |
| 50 | 8 |

*Calculated using Abbott's formula for untreated mortality rate of 10% (Abbott, W. S., "Method of Computing the Effectiveness of an Insecticide", Journal of Economic Entomology, 18(2), pp. 265-267 (1925)).

2 and 3. Tobacco budworm topical/injection test

TABLE IV

| Staurosporine | % Mortality | |
|---|---|---|
| ($\mu$g) | Topical | Injection |
| 10 | 60** | — |
| 5 | 100 | 100 |
| 2.5 | 80 | 80 |
| 1.5 | 0 | 20 |
| 0.63 | — | 0 |

**Living worms were stunted

We claim:

1. A method for inhibiting insects which comprises contacting insects or the habitat thereof with an insecticidally effective amount of staurosporine.

2. The method of claim 1 wherein said insects are selected from the group consisting of cockroaches, beetles, spiders, silverfish, bedbugs, fleas, flea larvae, mosquitoes, boxelder bugs, mites, ants, centipedes, flies, lice, ticks, aphids, scale, leafhopper, southern armyworm, two-spotted spidermite, cabbage looper, bollworm, codling moth, beet armyworm, and tobacco budworm.

3. The method of claim 1 wherein said insects are chewing and sucking insects.

4. The method of claim 1 wherein said insects are members of the family lepidoptera.

5. The method of claim 1 wherein said insects are selected from the group consisting of tobacco budworm, beet armyworm, leafhopper and two-spotted spidermite.

6. The method of claim 1 wherein the staurosporine is applied to plants, plant parts or the habitat thereof.

7. The method of claim 1 wherein the staurosporine is applied at a rate of between about 100 grams and about 2 kilograms per hectare.

8. The method of claim 1 wherein the staurosporine is applied at a rate of between about 250 grams and about 1 kilogram per hectare.

9. The method of claim 2 wherein the staurosporine is applied at a rate of between about 100 grams about 2 kilograms per hectare.

10. The method of claim 2 wherein the staurosporine is applied at a rate of between about 250 grams and about 1 kilogram per hectare.

11. The method of claim 3 wherein the staurosporine is applied at a rate of between about 100 grams and about 2 kilograms per hectare.

12. The method of claim 3 wherein the staurosporine is applied at a rate of between about 250 grams and about 1 kilogram per hectare.

13. The method of claim 4 wherein the staurosporine is applied at a rate of between about 100 grams and about 2 kilograms per hectare.

14. The method of claim 4 wherein the staurosporine is applied at a rate of between about 250 grams and about 1 kilogram per hectare.

15. A method for inhibiting insects comprising contacting insects or the habitat thereof with a composition containing a pesticidal adjuvant and an insecticidally effective amount of staurosporine.

16. The method of claim 15 wherein the amount of staurosporine present in the composition is from about 1 percent to about 50 percent by weight.

17. The method of claim 15 wherein said insects are chewing and sucking insects.

18. The method of claim 15 wherein said insects are members of the family lepidoptera.

19. The method of claim 15 wherein said insects are selected from the group consisting of tobacco budworm, beet armyworm, leafhopper and two-spotted spidermite.

* * * * *